(12) United States Patent
Sacher et al.

(10) Patent No.: US 7,927,357 B2
(45) Date of Patent: Apr. 19, 2011

(54) ADJUSTABLE LENGTH IMPLANT

(75) Inventors: Ronald Sacher, Needham, MA (US); Christopher Ramsay, West Wareham, MA (US); Richard Techiera, North Dartmouth, MA (US)

(73) Assignee: DePuy Spine, Inc., Raynham, MA (US)

( * ) Notice: Subject to any disclaimer, the term of this patent is extended or adjusted under 35 U.S.C. 154(b) by 1151 days.

(21) Appl. No.: 11/050,137

(22) Filed: Feb. 2, 2005

(65) Prior Publication Data
US 2006/0195087 A1    Aug. 31, 2006

(51) Int. Cl.
*A61B 17/88*    (2006.01)

(52) U.S. Cl. .......................... 606/258; 606/259; 606/277

(58) Field of Classification Search .................... 606/61, 606/90, 276–278, 258, 259; 623/17.11–17.16
See application file for complete search history.

(56) References Cited

U.S. PATENT DOCUMENTS

| | | | | |
|---|---|---|---|---|
| 2,333,033 A * | 10/1943 | Mraz | ................................. | 606/57 |
| 3,900,025 A * | 8/1975 | Barnes, Jr. | ....................... | 606/71 |
| 4,034,746 A | 7/1977 | Williams | | |
| 4,386,603 A * | 6/1983 | Mayfield | ........................ | 606/105 |
| 4,611,582 A * | 9/1986 | Duff | ................................. | 606/258 |
| 4,658,809 A * | 4/1987 | Ulrich et al. | ..................... | 606/258 |
| 4,747,394 A * | 5/1988 | Watanabe | ....................... | 600/232 |
| 4,827,918 A * | 5/1989 | Olerud | ........................... | 606/258 |
| 4,926,849 A * | 5/1990 | Downey | .......................... | 602/34 |
| 4,929,247 A | 5/1990 | Rayhack | | |
| 4,931,055 A * | 6/1990 | Bumpus et al. | .................. | 606/60 |
| 5,129,903 A * | 7/1992 | Luhr et al. | ....................... | 606/71 |
| 5,133,716 A * | 7/1992 | Plaza | ............................... | 606/61 |
| 5,167,662 A * | 12/1992 | Hayes et al. | ................... | 606/916 |
| 5,290,288 A * | 3/1994 | Vignaud et al. | ................. | 606/61 |
| 5,468,241 A * | 11/1995 | Metz-Stavenhagen et al. | ............................. | 606/319 |
| 5,540,696 A | 7/1996 | Booth, Jr. et al. | | |
| 5,700,263 A * | 12/1997 | Schendel | ......................... | 606/57 |
| 5,885,283 A * | 3/1999 | Gittleman | ........................ | 606/57 |
| 5,899,903 A * | 5/1999 | Cotrel | ........................... | 606/279 |
| 6,113,600 A * | 9/2000 | Drummond et al. | .......... | 606/252 |
| 6,126,660 A * | 10/2000 | Dietz | .............................. | 606/61 |
| 6,332,887 B1 * | 12/2001 | Knox | ............................... | 606/87 |
| 6,432,108 B1 * | 8/2002 | Burgess et al. | ............... | 606/252 |
| 6,451,019 B1 | 9/2002 | Zucherman et al. | | |
| 6,648,891 B2 * | 11/2003 | Kim | ............................... | 606/86 B |
| 6,761,721 B2 * | 7/2004 | Burgess et al. | ............... | 606/252 |
| 7,011,658 B2 * | 3/2006 | Young | ............................ | 606/258 |
| 7,029,472 B1 * | 4/2006 | Fortin | ............................ | 606/60 |
| 7,066,938 B2 * | 6/2006 | Slivka et al. | .................. | 606/914 |
| 7,214,226 B2 * | 5/2007 | Alleyne | ........................ | 606/86 A |
| 7,744,634 B2 | 6/2010 | Farris | | |
| 2003/0167059 A1 * | 9/2003 | Young | ............................. | 606/61 |

FOREIGN PATENT DOCUMENTS

WO    WO 0072768 A1 *   12/2000

* cited by examiner

*Primary Examiner* — Eduardo C Robert
*Assistant Examiner* — Ellen C. Hammond
(74) *Attorney, Agent, or Firm* — Nelson Mullins Riley & Scarborough, LLP; Kevin J. Canning; EuiHoon Lee

(57) ABSTRACT

A method and apparatus for providing an adjustable length surgical implant is provided, wherein the surgical implant is readily adjustable by a surgeon using a surgical tool sized for use with the surgical implant. Adjustment of the surgical implant further requires a small incision through the skin prior to the adjustment of the length of the implant, such that the potential for infection is greatly reduces and the associated trauma of surgery is lessened for the patient.

16 Claims, 6 Drawing Sheets

ADJUSTABLE LENGTH IMPLANT

RELATED APPLICATIONS

The present invention relates to U.S. patent application Ser. No. 11/050,256 entitled "Adjustable Length Implant", filed on Feb. 2, 2005.

FIELD OF THE INVENTION

The present invention generally relates to an adjustable surgical implant of varying length, and more specifically related to a variable length adjustable surgical implant for use in scoliosis correction.

BACKGROUND OF THE INVENTION

With the advent of biocompatible materials, the use of surgical implants in the correction of physical disorders has grown to become commonplace. These implantable devices are typically sized to be as unobtrusive as possible, while still maintaining the desired end result. Using such devices, numerous medical procedures can be accomplished that were impossible just years prior.

One type of implantable device is used in the correction of abnormal spinal curvature. Inherent in all human spines is some degree of curvature, as the spine is a highly flexible structure, capable of a high degree of movement and twist in a plurality of directions. Inherent in such flexibility, however, are instances where this curvature has becomes excessive. In such situations, the use of surgical implant devices becomes necessary.

One such example of excessive spinal curvature, namely lateral spinal deviation, is scoliosis. Scoliosis results in a sequential misalignment of the bones and intervertebral discs of the spine, and may result in pain, neurological disability or, in extreme cases, complete disability of a patient. The cause of scoliosis may be idiopathic in nature, may be due to congenital developmental disorders, or may be the result of a neuromuscular disease such as cerebral palsy.

A patient suffering from scoliosis will have a curved spine exhibiting a concave and a convex side. Scoliosis correction surgery generally requires that a plurality of hooks or screws are implanted into the spinal bones of a scoliosis patient. Attached to these hooks and screws are one or more adjustable rods, wherein the length of the rod can be varied. In correcting mild cases of scoliosis a rigid rod arrangement can be implanted along the concave side of the spine such that the rigid rod is used in maintaining the shape of the spine following a manual straightening. For example, during an invasive surgical procedure, a surgeon will manually straighten the spine and then tension the rigid rod arrangement along the concave side of the spine. Following the orientation of the rigid rod along the concave side of the spine, the newly straightened spinal column will typically retain the new shape. In cases where several manual straightenings are required, a second rigid rod may be implanted along the convex side of the spine to aid in maintaining the position of the corrected spinal column.

Existing spinal correction implants for use in correcting scoliosis typically have a mechanism wherein the length of the rods in the implants can be adjusted. Such adjustability is required because during the initial manual straightening the lengths of the rigid rods must be initially adjusted. Furthermore, when dealing with a patient requiring extensive spinal correction it is oftentimes necessary to approach total spinal straightening in stages. For example, an initial manual correction by a surgeon may be performed that roughly approximates the intended final position of the spine. After some period of time, a patient typically undergoes another surgical procedure where the spine is again manually straightened and the length of the attached rods readjusted. Existing implanted rod adjustment is currently performed using a ratcheting mechanism wherein a large incision is made such that the required ratcheting hardware can be inserted into the patient for use in adjusting the length of the rods.

Additionally, as scoliosis correction surgery is oftentimes performed on young patients, there exists a need to continually adjust the length of the surgically implanted rods as the patient grows and the length of the spinal column increases. Traditional correction techniques thereby require that the patient undergo continual invasive surgical procedures wherein the aforementioned ratcheting mechanism is used to adjust the length of the implanted surgical rods to correct for the lengthening of the spinal column of a growing patient. Such medical procedures oftentimes require large incisions to gain access to the rod adjusting mechanism and result in patient trauma and the risk of infections. In light of these facts, the time period between length adjustments of implanted surgical devices is oftentimes extended unnecessarily such that the patient does not need to undergo the pain and inconvenience of an invasive surgical procedure.

SUMMARY OF INVENTION

In light of the inherent problems regarding existing variable length surgical implants, a need exists for a system and method that allows incremental adjustments in implanted surgical devices wherein a minimally invasive surgical procedure is required. Using a minimally invasive procedure, a patient is not adversely affected by large surgical incisions during adjustment of the surgical implant thereby reducing patient discomfort and the risk of infections. Furthermore, employing an adjustable surgical device that may be remotely adjusted in a minimally invasive manner results in a greater likelihood of a patient consenting to frequent adjustments of the device thereby offering greater medical benefit to the patient.

Using the present invention an implantable body is provided wherein the implantable body has an adjustable rod associated with the body. The adjustable rod of the present invention may be adjusted using a surgical tool, manipulated by a surgeon, such that the relative length of the adjustable rod may be readily changed. Following a change in length of the rod, a surgeon may further fix the length of the adjustable rod again using an external surgical tool that is not implanted in the body cavity of the patient.

Using the present invention in scoliosis corrective surgery, the implantable body of the adjustable surgical instrument is affixed to one or more rigid rods attached to regions of the spinal column of a patient. In one embodiment, one or more rods associated with the present invention may be affixed using clamps, hooks, screws or some combination thereof to permanently affix one or more rods to a patient. During the initial installation, a surgeon can manually straighten the spine of the patient and initially configure the length of the adjustable surgical implant as necessary. In a case where large spinal corrections are required, at a later date the surgeon may create a small incision over the region of the implantable body to gain access to the adjustment mechanism of the implant. Using a surgical tool, the surgeon can shorten or lengthen the implant as required. In light of this, a surgeon can perform minute corrections to a patient over several minimally invasive procedures such that a straightened spinal column can be had. Additionally, when used with pediatric spinal corrective surgery, where a patient is still growing, a surgeon can lengthen the surgical implant as required due to the lengthening of the spinal column of the patient. Again, the procedure for lengthening the implant is such that only a small incision is required, wherein the incision is minimally invasive for the patient. In light of this, a patient is likely more inclined to undergo small incremental lengthening of the implant numerous times, as opposed to an invasive surgical procedure necessary using the prior art.

In accordance with one embodiment of the present invention, the adjustable rod of the surgical implant can contain a set of gear teeth disposed along a region of its length. These gear teeth are sized and orientated to mesh with a pinion gear provide within the implantable body, such that a traditional rack and pinion arrangement is provided. The provided pinion gear further includes a recessed region sized for accepting an external adjusting mechanism. For example, the recess of the pinion gear may be shaped to accept a Torx® style driver assembly. One skilled in the art will further recognize that numerous examples exist for use in transmitting mechanical energy to the adjusting pinion of the present invention.

Further associated with the implantable body is a second rod, wherein the second rod is fixed in nature and further affixed to a region of the patient. For example, the adjustable first rod may be affixed to a first region of a patient's bone, while the second fixed rod may be attached to an adjacent region of the patient's bone. Uses of the present invention, as understood by on skilled in the art, include but are not limited to scoliosis correction, kyphosis correction, and long bone fractures.

Following the adjustment of the length of the surgical implant, the surgeon may fix the length of the surgical implant such that the adjustable first rod does not move unnecessarily. This fixing of the adjustable rod can be completed using a various means including a set screw arrangement located within the implantable body. One skilled in the art will readily recognize, however, that numerous forms of length adjusting mechanisms, and adjustable rod affixing mechanism can be employed for use with the present invention. For example, in fixing the length of the adjustable rod a jam nut arrangement can be employed for use along the length of the adjustable rod such that the length can be adequately affixed in a semi-permanent manner.

In an alternate embodiment of the present invention a surgical implant for use in scoliosis correction of a spinal column is recited. In use, a first rod is affixed to the upper thoracic region of the spinal column of a patient. In mild scoliosis corrections, this first rod may initially be connected to the concave region of the spine. Disposed along a portion of the length of the first rod is a set of gear teeth. The first rod is associated with an implantable body, which contains a pinion assembly, wherein the pinion assembly meshes with the gear teeth of the forts adjustable rod such that a rack and pinion mechanism is formed. Upon rotation of the pinion, therefore, the rack, represented by the first rod, is free to move in or out of the implantable body such that the overall length of the apparatus changes. Rotation of the pinion may be provided using a surgical tool, operated by a surgeon, that meshes with a region of the pinion gear such that rotational energy can be provided to the pinion. A second rod is further attached to the lumbar region of a patient's spine, and associated with an implantable body. During a scoliosis surgical procedure, an initial incision is made such that the first and second rods, both associated with the implantable body, can be attached to specific regions of the spine. A manual spinal correction can then be performed by the surgeon and the length of the surgical implant adjusted accordingly.

As the present invention is intended for subcutaneous implantation in a patient, the use of biocompatible materials is in order. For example, the present invention can be constructed of surgical grade stainless steel, titanium, or numerous plastics exhibiting the requisite properties. One skilled in the art will readily recognize that this is not an exhaustive list of applicable materials and is solely present to provide examples of acceptable materials for use in constructing the present invention.

Following an initial manual spinal correction, and adjustment of the rods associated with the implantable body, the adjustable rod may be affixed in place using a mechanical fastening device. Such a device may take numerous forms, including but not limited to a set screw arrangement. Furthermore the set screw may be sized such that the adjusting instrument used by a surgeon to adjust the length of the device may further be used to operate the set screw. Additionally, the second rod may further be retained within the implantable body using a similar means or may be permanently affixed to the implantable body during construction.

In an alternate embodiment of the present invention, a method is recited for providing an adjustable surgical implant. In accordance with the method an implantable body is initially provided, wherein an adjustable rod is associated with the implantable body. Further associated with the implantable is an adjusting mechanism, such that the adjusting mechanism can be used in altering the length of the surgical implant. The altering of the length of the surgical implant can be accomplished using numerous means, including but not limited to a rack and pinion arrangement, wherein a surgeon can operate the pinion gear such that a rack associated with the adjustable rod can move relative to the implantable body.

In accordance with another aspect of the present invention, a method for correcting scoliosis of the spine is recited, wherein an implantable body is provided. Associated with the implantable body is a first adjustable rod attached to the upper portion of the spinal column and a fixed second rod attached to the lower portion of the spinal column. Upon operation of a pinion gear associated with the implantable body, and meshed with a rack mechanism along a portion of the first adjustable rod, the overall length of the surgical device can be altered to accommodate necessary changes in the device. Changes such as these may occur do to spinal corrections in the patient or due to growth of an pediatric surgical patient.

BRIEF DESCRIPTION OF THE DRAWINGS

The present invention is best understood with reference to the following description and accompanying drawings, wherein.

DETAILED DESCRIPTION

Figure 1:
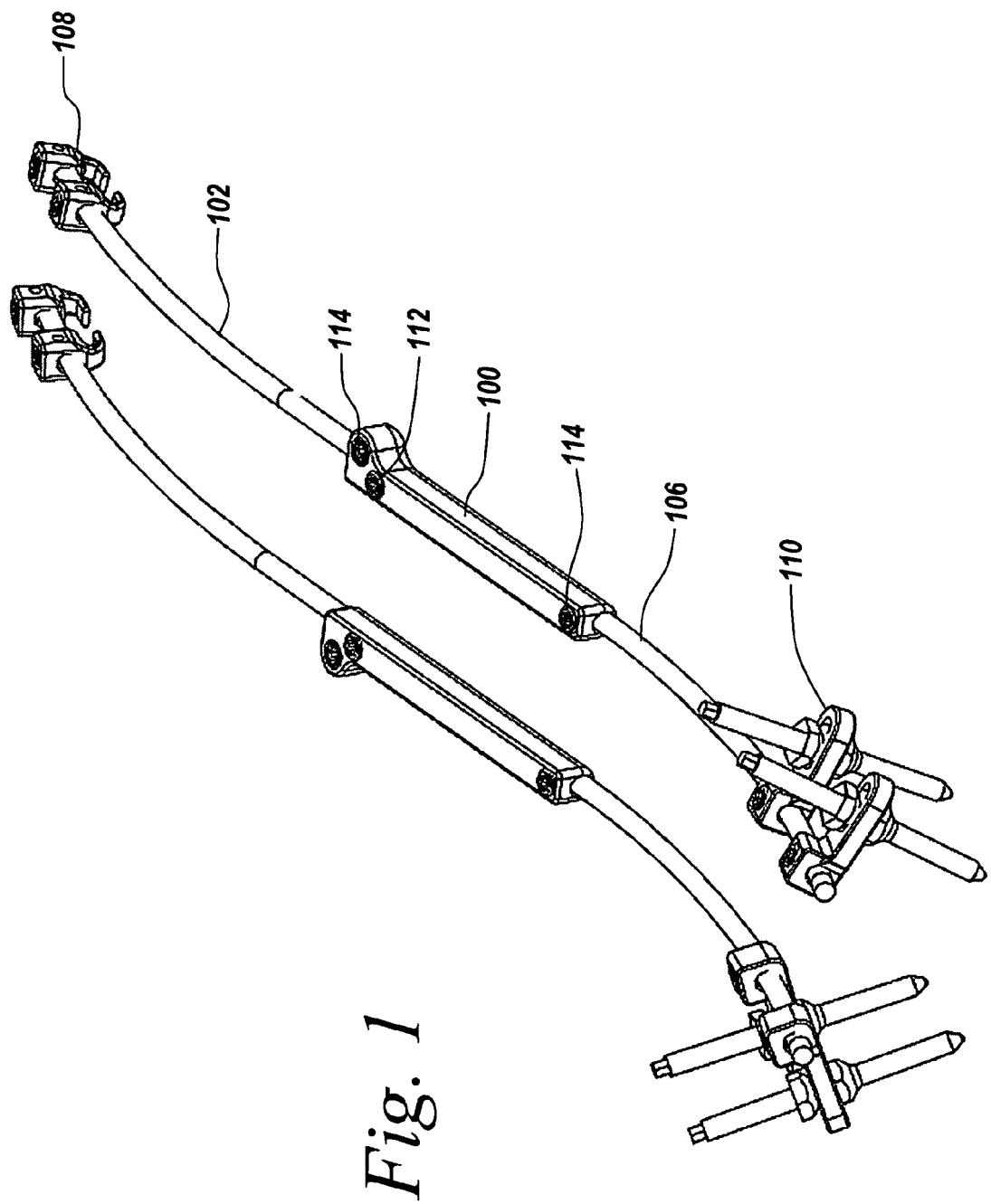
FIG. 1 shows an illustrative embodiment of the present invention for use in spinal correction surgery.

The present invention generally relates to an adjustable surgical implant of varying length, wherein the length of the surgical implant can be readily adjusted and more specifically related to a variable length adjustable surgical implant for use in scoliosis correction.

Using the present invention during a subcutaneous surgical procedure, should future adjustments to the length of the surgical implant be required, a small incision in the region of the adjusting mechanisms of the surgical apparatus is all that is required for adjustment to the length, thereby eliminating the need for large incisions and extensive surgical procedures.

FIGS. 1 through 6, wherein like parts are designated by like reference numerals throughout, illustrate an example embodiment of a variable length surgical implant according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 of the present invention is an illustrative embodiment of one aspect of the present invention when used in spinal correction surgery. While described in the context of a spinal correction surgical procedure, the present invention may be utilized in numerous surgical endeavors as understood by one skilled in the art, where a readily adjustable variable length surgical implant is required. Furthermore, as the present invention is suitable for subcutaneous implantation within a patient, the surgical implant 100 is constructed of a biocompatible material such that adverse infection or rejection by a patient's body does not occur.

As illustrated in FIG. 1, an implantable body 100 is in communication with an adjustable rod 102. In the present embodiment further associated with the implantable body 100 is a second fixed length rod 106 affixed to the implantable body 100. The second rod 106 may be permanently affixed to the implantable body 100 during manufacture of the surgical implant 100, or may be inserted into the implantable body 100 by a surgeon and retained using a mechanical fastening means 114. For illustrative purposes, the present embodiment illustrates a set screw arrangements for use as a mechanical fastening means 114 for retaining the second rod 106. While useful for illustrative purposes, the use of a set screw arrangement is not intended to limit the potential mechanical fasting means which may be employed with the present invention.

In one embodiment, the second rod 106 may be attached to the spinal column of a patient using anchoring screws 110. Furthermore, while used in spinal correction surgery, the adjustable rod 102 may be affixed to a region of the spinal column of a patient using a clamping mechanism 108. Such anchoring screws 110 and clamping mechanisms 108 are well known by those skilled in the art when used during spinal surgery. In use the surgical implant 100 may be positioned along a concave or convex region of a patient's spine such that the surgical implant 100 is located just below the skin of the patient. Additionally, should several corrections be required in a patient, two or more surgical implants 100 in accordance with the present invention may be oriented along various region of the spinal column of a patient.

Following orientation of the surgical implant 100 of the present invention, an initial length is set by a surgeon. This initial length represents the length required after a manual manipulation of the spinal column of a patient. Following an initial manual manipulation and associated initial length determination, it oftentimes becomes necessary to adjust the length of the surgical implant 100 later in time. For example, following the growth of a pediatric patient, wherein the length of the spinal column increases, it is necessary to readjust the surgical implant 100 to compensate for such growth. In light of this, an adjusting mechanism 104 is provided. The adjusting mechanism of the present invention may take numerous forms, such that the surgical implant 100 may be readily adjusted using a minimally invasive procedure. For illustrative purposes the adjusting mechanism of the present invention is illustrated as a rack and pinion arrangement, as detailed in FIG. 2.

Figure 2:
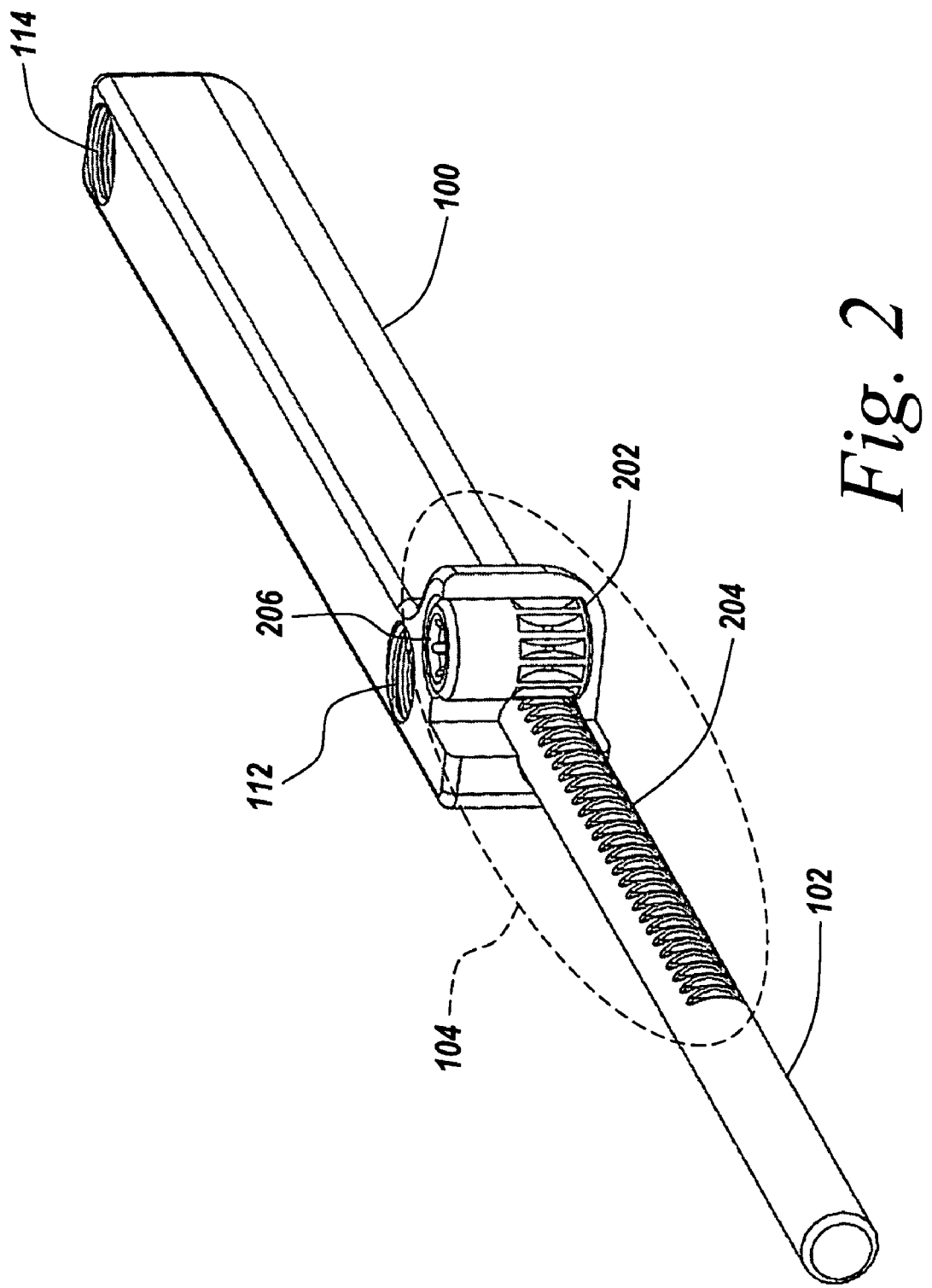
FIG. 2 shows the adjustable length implantable body of FIG. 1 in more detail.

The adjusting mechanism of FIG. 2 includes a pinion gear 202 associated with the implantable body 100. The pinion gear is further associated with a set of gear teeth 204 disposed along a portion of the adjustable rod 102 such that said teeth form a rack mechanism. The gear teeth 204 disposed along a portion of the adjustable rod 102 are sized and orientated to mesh with the pinion gear 202 provided. Operating the adjusting mechanism 104, made of the gear teeth 204 and pinion gear 202, thereby allows for the linear motion of the adjustable rod 102 relative to the implantable body 100 and the subsequent change in length of the surgical implant 100.

Operation of the pinion 202 gear may be provided using a surgical instrument (not shown) sized to mate with a hollow recess 206 located within a region of the pinion gear. This hollow recess 206 may take numerous forms, as understood by one skilled in the art, such that a rotational motion of the surgical tool, provided by a surgeon, can be transmitted to the pinion gear 202. In one embodiment, the hollow recess 206 of the present invention included numerous groves along its length such that a correspondingly shaped surgical tool (not show) can mate with said grooves to allow for power transmission to the pinion gear 202. One such example of a suitable hollow recess 206 configuration is a Torx® shaped recess, wherein a mating Torx® driver can be employed to cause the pinion 202 to rotate. In the alternative, the hollow recess 206 may be eliminated so long as a means for delivering rotational energy to the pinion 202 is provided.

Following the rotation of the pinion 202, and the subsequent change in length of the adjustable rod 102, a surgeon may lock the length of the adjustable rod 102 using a mechanical fastening means. In one embodiment, the mechanical fastening means can be a set screw 112 disposed above the adjustable rod 102 such that upon tightening of the set screw 112 the adjustable rod 102 is captured within the implantable body 100 of the present invention. The set screw 112 for use in the illustrative embodiment may further included a hollow recess (not shown) disposed within the set screw 112 which conforms to the hollow recess 206 provided in the pinion gear 202. Using such an arrangement, a surgeon can use the same surgical tool (not shown) to adjust both the pinion gear 202 as well as the set screw 112. One skilled in the art will recognize, however, that the use of a set screw 112 is solely for illustrative purposes and numerous alternative mechanical fastening means may be employed in retaining the adjustable rod 102 such that the length of the adjustable rod 102 remains constant.

Orientation of the implantable body 100 of the present invention is such that the hollow recess 206 of the pinion gear 202 is oriented toward the surface of the patient skin. In light of this, when the need arises to adjust the length of the surgical implant 100, a surgeon simply needs to locate the hollow recess 206 of the pinion gear 202 and provide a small incision through the patients skin in the area of the hollow recess 206 of the pinion gear 202 and mechanical fastening means 112. Location of the implantable body 100 and hollow recess 206 is typically easily accomplished as in use the surgical implant 100 is generally located just below the patient's skin. Following such a small incision, the mechanical fastening means 112 may be loosened using a surgical tool, and the pinion gear 202 rotated to cause a lengthening or shortening of the adjustable rod 102 of the surgical implant 10. When the appropriate length is achieved, the surgeon tightens the mechanical fastening means 114 such that the adjustable rod 102 does not move out of position. During surgical procedures wherein frequent adjustment of the surgical implant 100 is required, a subcutaneous port may be provided thorough the patients skin in the area of the implantable body 100 such that frequent incisions through the skin are no longer necessary. Such subcutaneous ports are well known by those skilled in the art.

Figure 3:
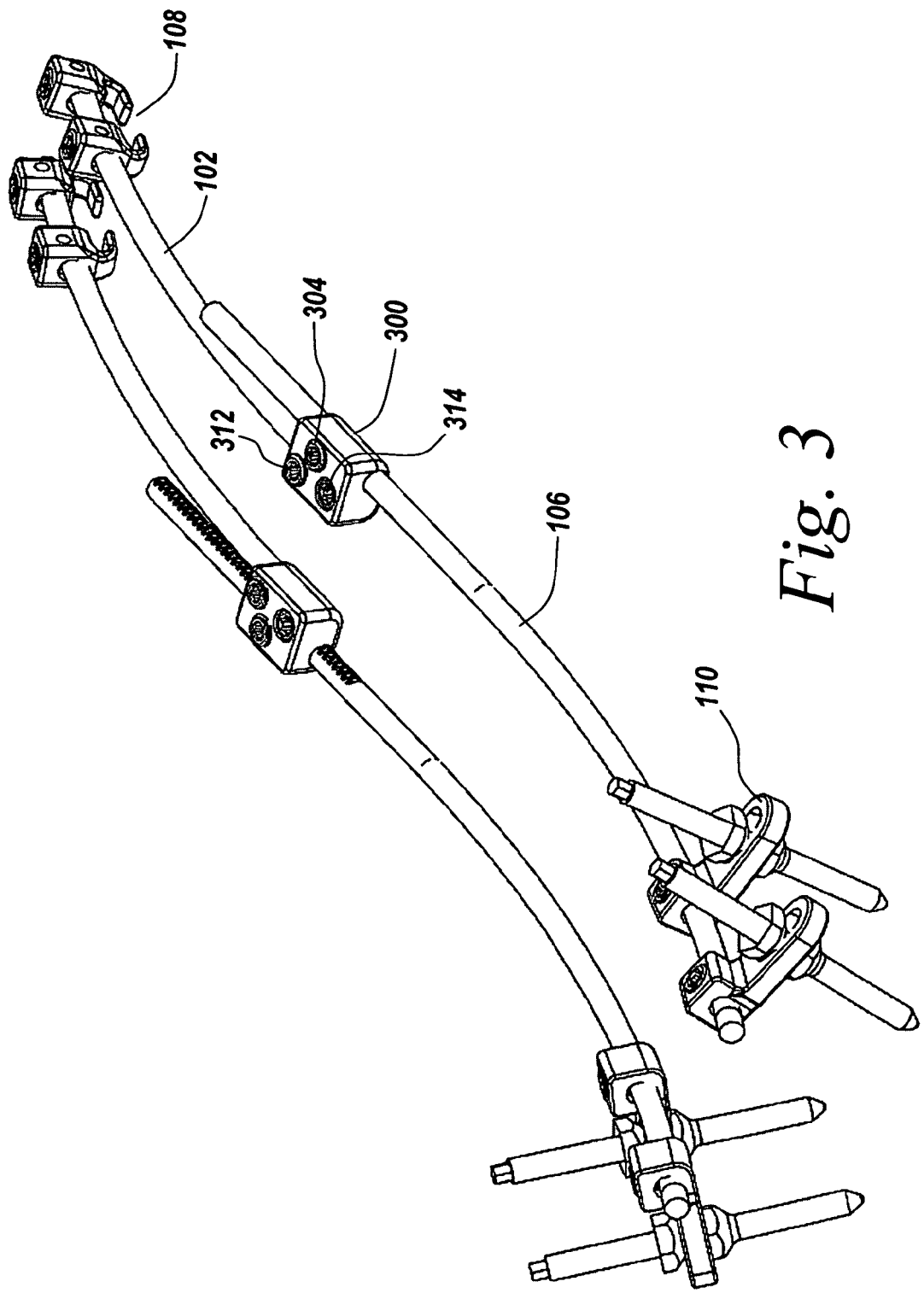
FIG. 3 shows an alternative embodiment of the adjustable length implantable body of the present invention.

FIG. 3 shows an alternative illustrative embodiment used in spinal correction surgery where an adjustable length implant is required. For illustrative purposes the surgical implant 300 of FIG. 3 is arranged for use in spinal correction surgery. Such an arrangement is for illustrative purposes only, and is not intended to limit the scope of use of the present invention. The implantable body 300 of FIG. 3 is such that the adjustable rod 102 and the second fixed rod 106 are located in a side by side arrangement. Following adjustment of the adjustable rod 102 using an adjusting mechanism 304 the adjustable rod 102 moves past the fixed second rod 106. The fixed second rod 106 may be permanently affixed to the implantable body 300 or may be inserted and locked into place by a surgeon using a mechanical fastening device 314. Furthermore, following adjustment of the length of the adjustable rod 102, the adjustable rod may be affixed in place using a mechanical fastening device 312.

Figure 4:
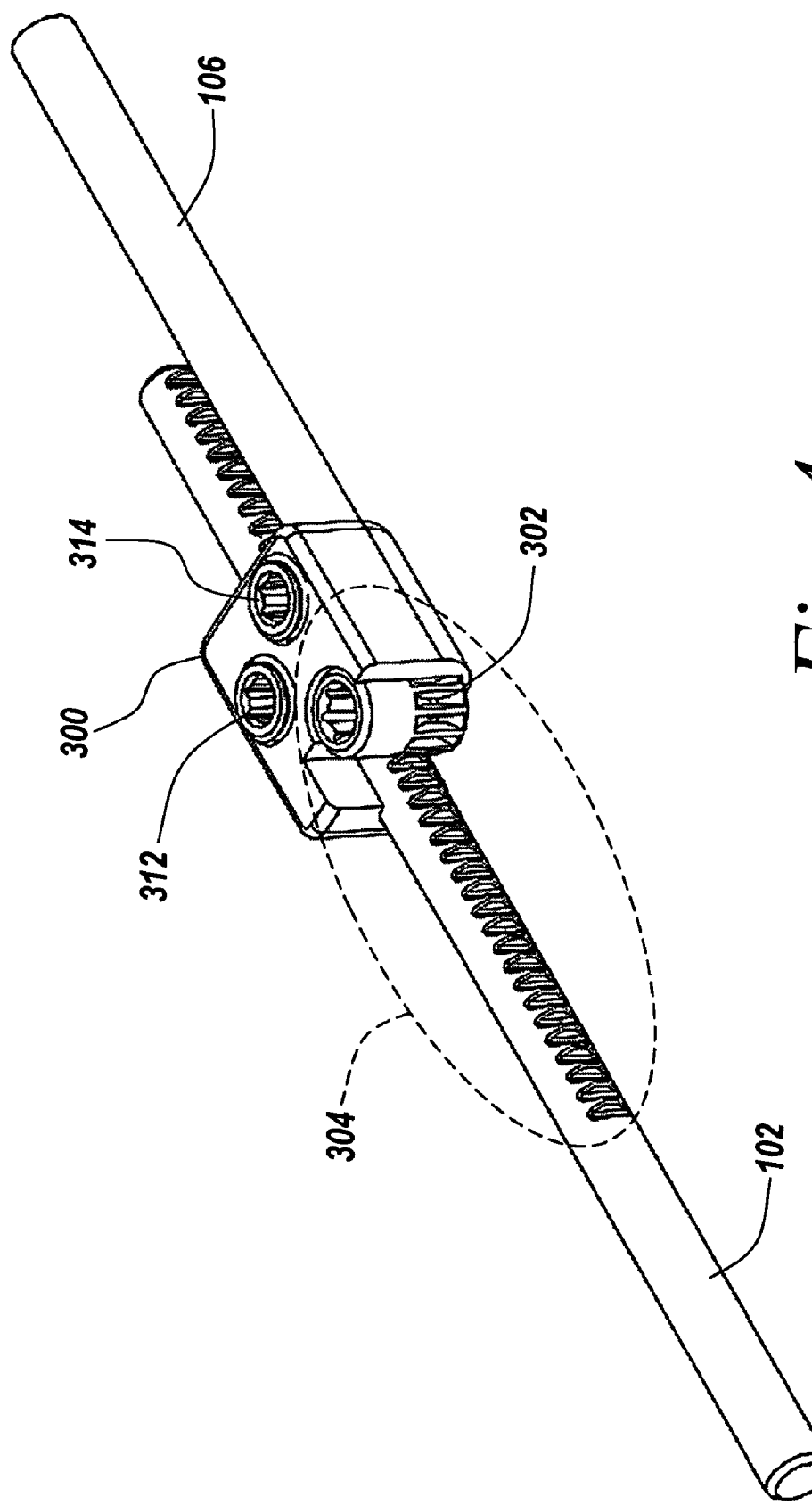
FIG. 4 shows the adjustable length implant of FIG. 3 in more detail.

FIG. 4 shows an enlarged view of the implantable body 300 and the adjustable rod 102. The arrangement in FIG. 4 is such that the fixed second rod 106 and the adjustable rod 102 are located in a side by side arrangement. Such an arrangement offers the benefit of a decreased implantable body 300 size such that the surgical implant 300 is less obtrusive when implanted in a patient. For illustrative purposes a rack and pinion mechanism is shown for altering the length of the adjustable rod 102. Along a portion of the adjustable rod 102 are a set of gear teeth 304 which are sized and orientated to mate with a pinion gear 302 located within the implantable body 300 of the present invention. Upon the provision of a mechanical force on the pinion gear 302 by a surgeon using a surgical tool (not shown) the pinion gear can rotate such that the length of the adjustable rod 102 is altered. Furthermore, the adjustable rod 102 may be affixed in place using a mechanical fastening device 314, such as a set screw, when the appropriate length is determined.

Figure 5:
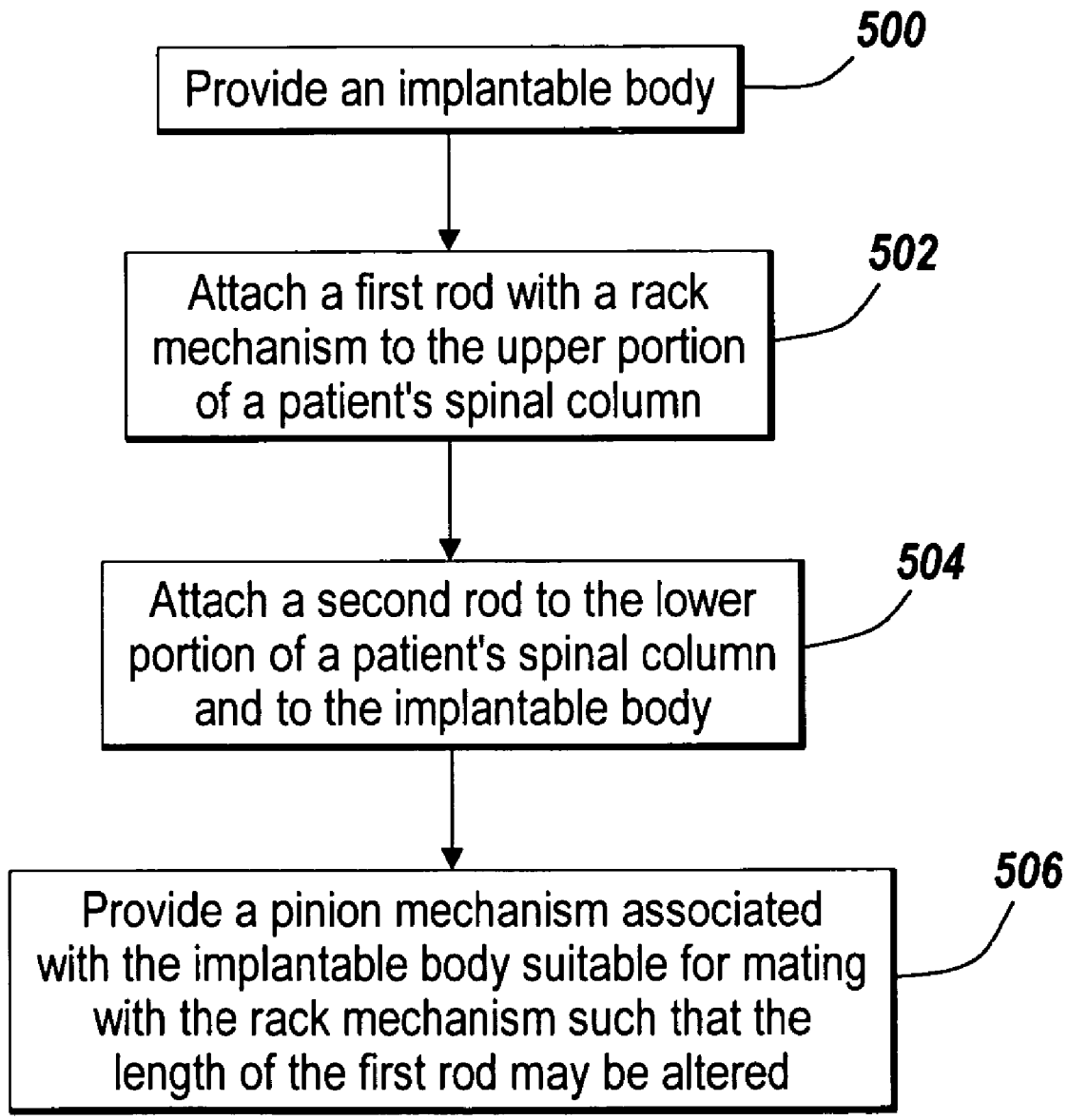
FIG. 5 is a flowchart illustrating the steps required in using the present invention in scoliosis corrective surgery wherein an adjustable surgical implant is provided.

FIG. 5 is a flowchart illustrating the steps required in using the present invention in scoliosis corrective surgery wherein an adjustable surgical implant is provided. In accordance with step 500 of FIG. 5, an implantable body is first provided. This implantable body can be manufactured of a biocompatible material suitable for implantation into the body of a patient such that an adverse patient reactions does not occur. Furthermore, in accordance with step 502 a first rod containing a rack mechanism disposed along a portion of the rod is attached to the upper spinal region of a patient. When used in scoliosis corrective surgery, this upper thoracic spinal region may be located on a concave region, a convex region, or some combination thereof of the patient's spinal column. Additionally a second rod is attached to the lumbar region of a patient's spinal column, wherein the second rod is further associated with the implantable body, in accordance with step 504. The second rod may be attached to the lower portion of the spinal column using various means, including but not limited to clamps, spinal fasteners and screws. In accordance with step 506, a pinion mechanism associated with the implantable body is provided, wherein the pinion mechanism mates with the rack mechanism of the first rod such that the length of the rod may be altered. The alteration of the length of the first rod, using the rack and pinion mechanism, can be accomplished by a surgeon using a surgical tool sized to mate with the pinion of the present invention. Furthermore, following the setting of the appropriate length of the adjustable rod, a mechanical fastening apparatus may be employed to affix the length of the adjustable rod such that it does not move unintentionally. One such example of an appropriate fastening device is a traditional set screw means, as understood by one skilled in the art.

Figure 6:
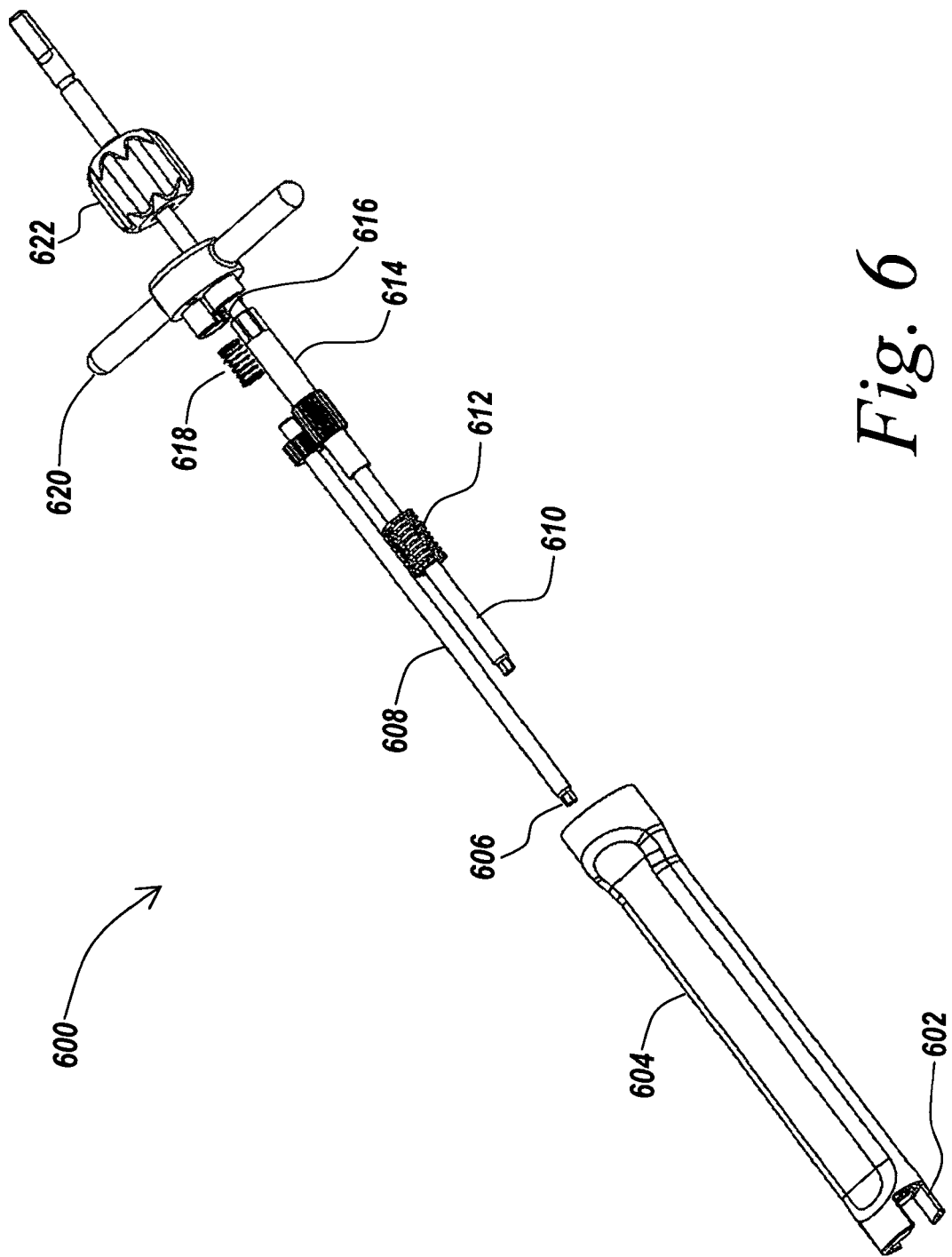
FIG. 6 is an illustrative example of a surgical device suitable for use in altering the length the surgical implant of the present invention.

FIG. 6 is an illustrative embodiment of a surgical device 600 for use with the present invention, wherein said surgical device 600 is sized and orientated to mate with the hollow recess provided in the pinion gear 202 illustrated in FIG. 2. In one embodiment, the surgical device 600 includes a housing 604 capable of containing both a pinion driver 608 and a set screw driver 610. Both the pinion driver 608 and set screw driver 610, when used in conjunction with the surgical implant of the present invention, provide a means by which the length of the surgical implant (not shown) may be adjusted. Further associated with the surgical device 600 is a torque transfer gear knob 622 which may be operated by a surgeon to provide an adjustment in the surgical implant.

In use the surgical device 600 is orientated over the surgical implant. As the surgical implant is typically orientated just below the skin of a patient, locating the position of the surgical implant is readily accomplished by a surgeon. Furthermore, a small incision through the patient's skin may be provided such that the housing centering feature 602 of the surgical device 600 may be located above the surgical implant. The housing centering feature 602 is sized and oriented such that it captures the geometry of the surgical implant allowing for subsequent adjustment in implant length.

Following capture of the surgical implant a surgeon can provide a downward force on the torque transfer knob 622 such that the pinion gear lock 616 is released. Upon release of the pinion gear lock 616 the torque transfer knob 622 is rotated until the pinion driver 608 settles into the recess provided in the pinion gear (not shown). The downward force provided on the torque transfer knob 622 is then released wherein the torque transfer gear 614 is locked into place by the locking mechanism 616 associated with the housing cap 620. Furthermore the pinion driver spring 618 exerts a force upon the pinion driver 608 and associated pinion driver mechanism 606 such that the pinion driving mechanism 606 will engage the recess in the pinion of the surgical implant (not shown) when the pinion driving mechanism 606 and the pinion gear recess are correctly orientated.

The setscrew driver 610 is then inserted into the setscrew of the surgical implant such that the setscrew of the surgical implant can be loosened. Following the loosening of the setscrew of the surgical implant the length of the surgical implant can be adjusted. Such an adjustment can be accomplished by pushing downward on the torque transfer knob 622 and rotating the torque transfer knob 622 appropriately. For example, clockwise rotation of the torque transfer knob 622 relative to the surgical implant can result in the shortening of the implant length, while counterclockwise rotation of the torque transfer knob 622 results in a lengthening of the implant. One skilled in the art will readily recognize that the aforementioned relationship between torque transfer knob 622 rotation and implant length can be readily reversed as dictated by the needs of the surgeon or medical procedure. After the appropriate adjustment to the implant length has been accomplished, the setscrew associated with the surgical implant is subsequently tightened, using the setscrew driver 610, such that the length of the surgical implant remains constant. A surgeon may now remove the surgical device 600 and subsequently close the incision using any number of means as understood by one skilled in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. An adjustable surgical implant, said implant comprising:
   an elongated implantable body having a rectangular shape and including a first end having a first opening and an opposed second end having a second opening
   an adjustable cylindrical rod, associated with the first end of the implantable body such that a length of the adjustable cylindrical rod relative to the implantable body is adjustable, wherein a set of gear teeth are disposed on a portion of the adjustable cylindrical rod to form a rack mechanism;
   a second cylindrical rod affixed to the second end of the implantable body such that a length of the second cylindrical rod relative to the implantable body is fixed;
   an anchoring screw disposed at an end of the second cylindrical rod to anchor the second cylindrical rod to a spinal column;
   an adjusting mechanism disposed at the first end of the implantable body and meshing with the rack mechanism of the adjustable cylindrical rod, wherein the adjusting mechanism is alterable following implantation of the surgical implant to adjust the length of the adjustable cylindrical rod relative to the implantable body while the length of the second cylindrical rod relative to the implantable body is unchanged;
   wherein an end of the adjustable cylindrical rod is positioned between the first end and the second end of the implantable body as the length of the adjustable cylindrical rod relative to the implantable body is adjusted.

2. The adjustable surgical implant of claim 1, wherein the adjusting mechanism is a pinion gear.

3. The adjustable surgical implant of claim 2, wherein the pinion gear further comprises a recessed region, said recessed region configured for receiving a remote adjustment implement used in rotating the pinion gear.

4. The adjustable surgical implant of claim 1, wherein the second rod is affixed to the implantable body using a mechanical fastening means.

5. The adjustable surgical implant of claim 4, wherein the mechanical fastening means for affixing the second rod is a set screw.

6. The adjustable surgical implant of claim 1, wherein the adjustable rod can be affixed in position using a mechanical fastening means.

7. The adjustable surgical implant of claim 6, wherein the mechanical fastening means is a set screw.

8. The adjustable surgical implant of claim 1, further comprising a remote adjustment implement, wherein said implement provides mechanical energy to the adjusting mechanism for uses in changing the length of the adjustable surgical implant.

9. An adjustable surgical implant for use in scoliosis correction of a spinal column, said implant comprising:
   an elongated implantable body having a rectangular shape and including a first end having a first opening and an opposed second end having a second opening
   a first cylindrical rod coupled to the first end of the implantable body such that a length of the first cylindrical rod relative to the implantable body is adjustable, wherein the first cylindrical rod comprises a rack mechanism disposed on a portion of the first cylindrical rod;
   a clamping mechanism disposed at a first end of the first cylindrical rod to clamp the first cylindrical rod to an upper thoracic region of a spinal column;
   a second cylindrical rod associated with the second end of the implantable body such that a length of the second cylindrical rod relative to the implantable body is fixed;
   an anchoring screw disposed at an end of the second cylindrical rod to anchor the second cylindrical rod to a lumbar region of the spinal column;
   a pinion mechanism associated with the first end of the implantable body, wherein said pinion mechanism is configured to mesh with the rack mechanism of the first cylindrical rod to provide post implantation adjustment of the surgical implant, the pinion mechanism being configured to adjust the length of the first cylindrical rod relative to the implantable body while the length of the second cylindrical rod relative to the implantable body is unchanged,
   wherein a second end of the first cylindrical rod is positioned between the first end and the second end of the implantable body as the length of the first cylindrical rod relative to the implantable body is adjusted.

10. The surgical implant of claim 9, wherein said implant is constructed of a biocompatible material.

11. The adjustable surgical implant of claim 9, wherein the second rod is retained within the implantable body using a mechanical fastening means.

12. The surgical implant of claim 11, wherein the mechanical fastening means is a set screw.

13. The surgical implant of claim 9, wherein the location of the first rod relative to the implantable body is fixed using a mechanical fastening means.

14. The surgical implant of claim 13, wherein the mechanical fastening means is a set screw.

15. The surgical implant of claim 9, wherein the pinion mechanism further comprises a recessed region, said recessed region configured for receiving a remote adjustment implement used in rotating the pinion gear.

16. The surgical implant of claim 9, further comprising a remote adjustment implement, wherein said implement provides mechanical energy to the adjusting mechanism for uses in changing the length of the adjustable surgical implant.

* * * * *